United States Patent [19]

Reiners et al.

[11] Patent Number: 4,952,241
[45] Date of Patent: Aug. 28, 1990

[54] (METH)ACRYLIC ACID DERIVATIVES CONTAINING URETHANE GROUPS

[75] Inventors: Jürgen Reiners, Leverkusen; Wolfgang Podszun; Jens Winkel, both of Cologne; Carlhans Süling, Odenthal; Gerhard Klein, Monheim, all of Fed. Rep. of Germany

[73] Assignee: Bayer Aktiengesellschaft, Leverkusen, Fed. Rep. of Germany

[21] Appl. No.: 379,128

[22] Filed: Jul. 13, 1989

Related U.S. Application Data

[62] Division of Ser. No. 72,467, Jul. 10, 1987.

[30] Foreign Application Priority Data

Jul. 25, 1986 [DE] Fed. Rep. of Germany ....... 3625202
Feb. 3, 1987 [DE] Fed. Rep. of Germany ....... 3703130

[51] Int. Cl.$^5$ ..................... A61C 13/087; A61K 6/08; C07C 271/00
[52] U.S. Cl. ................... 106/35; 433/202.1; 433/212.1; 433/217.1; 433/228.1; 523/115; 523/116; 525/920; 526/301; 560/26; 560/115; 560/158
[58] Field of Search ............ 106/35; 433/202.1, 212.1, 433/217.1, 228.1; 523/115, 116; 525/920; 526/301; 560/26, 115, 158

[56] References Cited

U.S. PATENT DOCUMENTS

| 4,243,578 | 1/1981 | O'Sullivan et al. | 433/228.1 |
| 4,347,174 | 8/1982 | Nagase et al. | 523/116 |
| 4,554,336 | 11/1985 | Kidd et al. | 526/301 |
| 4,813,875 | 3/1989 | Hare | 433/214 |
| 4,879,402 | 11/1989 | Reiners et al. | 560/26 |
| 4,904,750 | 2/1990 | Reiners et al. | 526/301 |

FOREIGN PATENT DOCUMENTS 1328232 8/1973 United Kingdom .

*Primary Examiner*—Paul Lieberman
*Assistant Examiner*—Linda D. Skaling
*Attorney, Agent, or Firm*—Sprung Horn Kramer & Woods

[57] ABSTRACT

The new (meth)acrylic acid derivatives containing urethane groups can be prepared by reaction of a (meth)acrylic acid ester with diisocyanates and subsequent reaction with polyols. The compounds can be used for dental materials.

7 Claims, No Drawings

(METH)ACRYLIC ACID DERIVATIVES CONTAINING URETHANE GROUPS

This is a division of application Ser. No. 072,467, filed 7-10-87.

The invention relates to new (meth)acrylic acid derivatives containing urethane groups, to their preparation and to their use as monomeric components for dental materials.

The use of polyfunctional (meth)acrylic acid derivatives as components for tooth-filling materials is known. Thus, in EP-A 0,017,936, acrylic acid esters and methacrylic acid esters of pentaerythritol are described. In combination with inorganic fillers, the monomers described therein provide dental materials which show undesired shrinkage on polymerization, causing the formation of a gap between the tooth material and the filling material.

In U.S. Pat. No. 4,554,336, (meth)acrylic acid derivatives containing urethane groups are described for adhesives in the dental field, wherein the urethane groups are substituted by a radical containing a (meth)acrylate group. These compounds as components in dental compositions show inadequate properties, in particular a strength which is too low for use in practice.

New (meth)acrylic acid derivatives, containing urethane groups, of the formula (I)

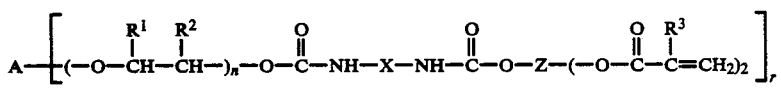

(I)

wherein
  A is a straight-chain or branched aliphatic radical having 2 to 20 carbon atoms and optionally containing 1 to 3 oxygen bridges, an aromatic radical having 6 to 24 carbon atoms, an araliphatic radical having 7 to 26 carbon atoms or a cycloaliphatic radical having 6 to 26 carbon atoms,
  r represents the number of chains starting from A and denotes a number from 2 to 6,
  $R^1$ and $R^2$ are identical and denote hydrogen or are different and denote hydrogen and methyl, n denotes a number from 0 to 5, independently for each chain starting from A,
  X is a divalent, straight-chain or branched aliphatic radical having 2 to 24 carbon atoms, an aromatic radical having 6 to 26 carbon atoms, an araliphatic radical having 7 to 26 carbon atoms or a monocycloaliphatic radical having 6 to 26 carbon atoms, it being possible for the aliphatic, aromatic, araliphatic and/or monocycloaliphatic radicals to contain 1 to 2 oxygen bridges and for several of the aliphatic, aromatic, araliphatic and/or monocycloaliphatic radicals to be linked via optionally substituted methylene groups,
  Z denotes a trivalent, straight-chain or branched aliphatic hydrocarbon radical which has 3 to 15 carbon atoms, can optionally contain 1 to 3 oxygen bridges and can optionally be subsstituted by 1 to 3 additional (meth)acrylate radicals, and
  $R^3$ denotes hydrogen or methyl, independently for each chain starting from A.

Dental materials which are based on the (meth)acrylic acid derivatives, according to the invention, containing urethane groups, surprisingly show substantially less shrinkage on polymerization and a higher strength, and they are therefore particularly suitable for use in practice.

Within the scope of the present invention, the substituents can have the following meanings:

An aliphatic radical (A) can be a straight-chain or branched hydrocarbon radical having 2 to 20, preferably 3 to 12, carbon atoms. The following aliphatic radicals may be mentioned as examples:

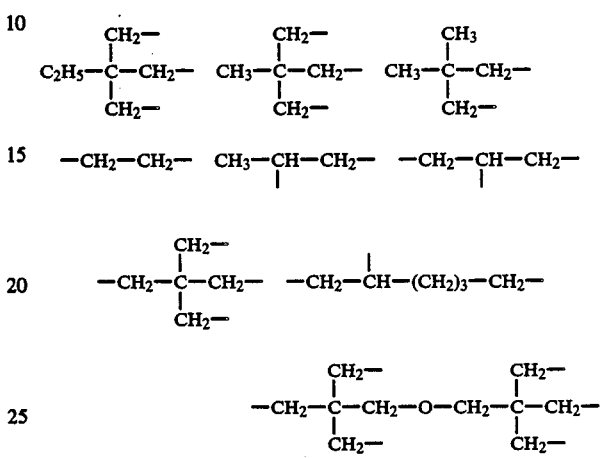

An aromatic radical (A) can be an aromatic hydrocarbon radical having 6 to 24, preferably 6 to 14, carbon atoms. The following aromatic radicals may be mentioned as examples:

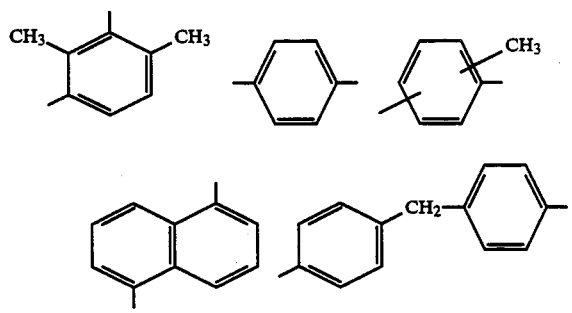

An araliphatic radical (A) can be a hydrocarbon radical having 7 to 26 carbon atoms with a straight-chain or branched aliphatic part and an aromatic part, the aromatic part preferably having 6 to 12 carbon atoms and the aliphatic part preferably having 1 to 14 carbon atoms. The following araliphatic radicals may be mentioned as examples:

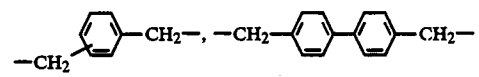

-continued

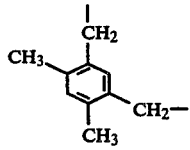

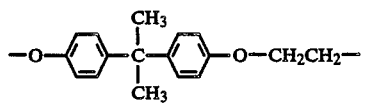

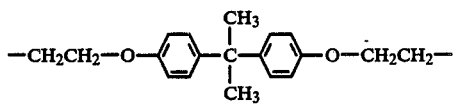

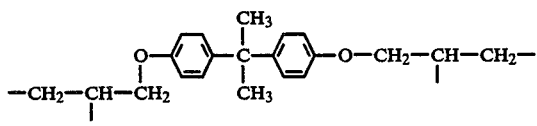

A cycloaliphatic radical (A) can be a cyclic hydrocarbon radical having 6 to 26 carbon atoms, preferably 6 to 14 carbon atoms. The following cycloaliphatic radicals may be mentioned as examples:

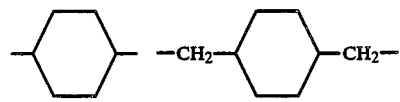

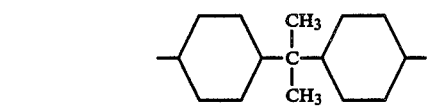

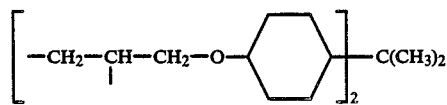

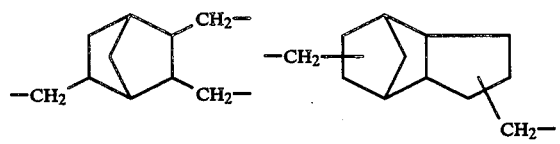

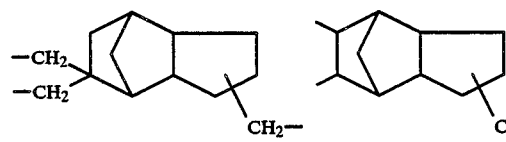

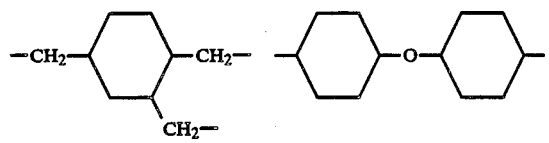

The radicals A can contain 1 to 2, preferably 1, oxygen atoms, preferably in the aliphatic or cycloaliphatic part, so that, for example, they represent aliphatic or cycloaliphatic ethers.

The following radicals A may be mentioned as particularly preferred: ethylene, propylene, 2,2-bismethylenebutan-1-yl, 2,2-bismethylene-propan-1-yl, 2,2-bis-methylenepropane-1,3-diyl, 1,1'-oxy-bis-[(2,2-methylene)-propane-1,3-diyl], propane-1,2,3-triyl, 1,6-hexamethylene, 1,4-tetramethylene, 1,4-phenylene, xylylene, 1,4-cyclohexylene, 1,4-bismethylene-1,4-cyclohexane, 2,2-bis-(1,4-phenylene)propane, 3(4),8(9)-bismethylene-tricyclo[5.2.0$^{2,6}$]decane and isomers thereof, and 4(5),9-bismethylene-3,8-dimethyltricyclo[5.2.1.0$^{2,6}$]decane.

The radicals 2,2-bismethylene-butan-1-yl, propane-1,2,3-triyl, 2,2-bismethylenepropane-1,3-diyl and 3(4),8(9)-bismethylene-tricyclo[5.2.1.0$^{2,6}$]decane are particularly preferred.

A divalent, straight-chain or branched aliphatic radical (X) can denote a hydrocarbon radical having 2 to 24 carbon atoms, preferably 2 to 12 carbon atoms. The following divalent aliphatic radicals may be mentioned as examples: ethylene, propylene, 1,4-tetramethylene, 1,6-hexamethylene or 2,2,4-trimethyl-1,6-hexamethylene and isomers.

A divalent aromatic radical (X) can denote an aromatic hydrocarbon radical having 6 to 26, preferably 6 to 18, carbon atoms. The following aromatic radicals may be mentioned as examples:

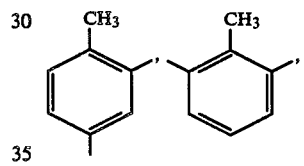

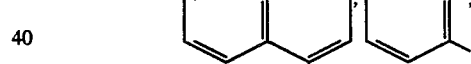

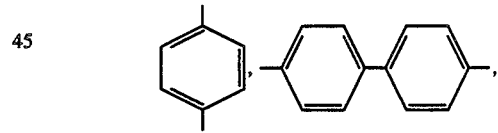

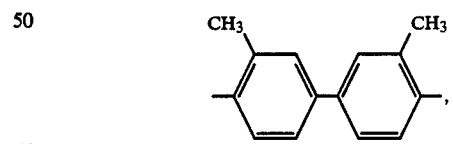

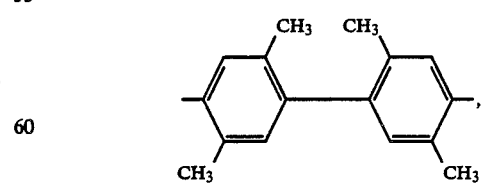

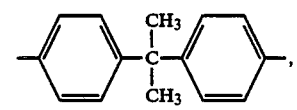

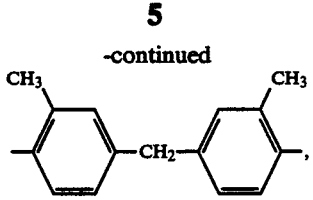

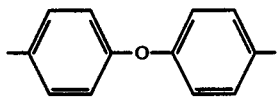

A divalent araliphatic radical (X) can denote a hydrocarbon radical having a straight-chain or branched aliphatic part and an aromatic part, having 7 to 20 carbon atoms, the aromatic part preferably having 6 to 12 carbon atoms and the aliphatic part preferably having 1 to 8 carbon atoms. The following araliphatic radicals may be mentioned as examples:

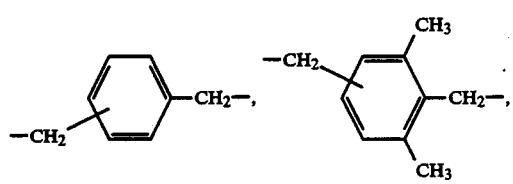

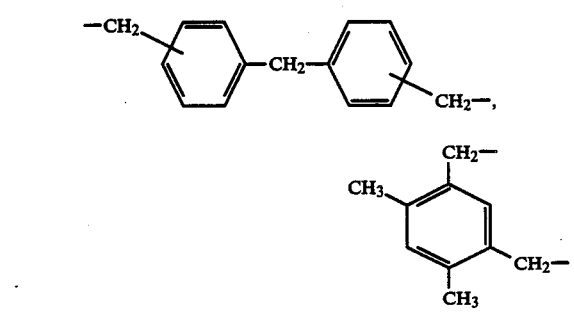

A divalent monocycloaliphatic radical (X) can denote a hydrocarbon radical having 6 to 26, preferably 6 to 14, carbon atoms. The following may be mentioned as examples:

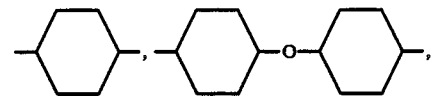

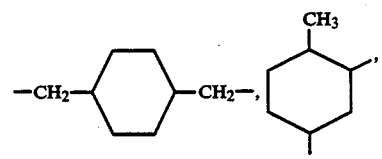

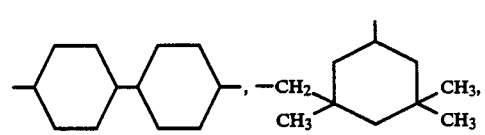

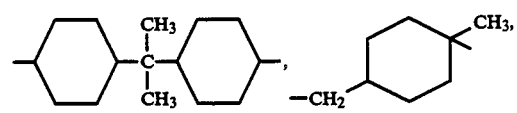

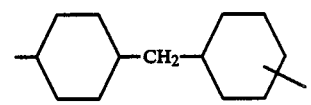

It is also possible for several (preferably 1 to 3) of the aromatic, araliphatic and/or monocycloaliphatic radicals mentioned to be linked via optionally substituted methylene groups.

Examples of optionally substituted methylene groups can be the groups

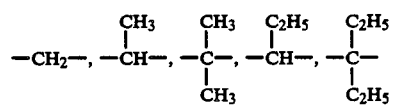

A trivalent hydrocarbon radical (Z) can be a straight-chain or branched aliphatic hydrocarbon having 3 to 15 carbon atoms, preferably 3 to 10 carbon atoms. Optionally, the radical Z can contain 1 to 3 oxygen bridges, preferably 1 to 2 oxygen bridges. It is also possible for the radical Z to be substituted by 1 to 3, preferably 1 to 2, (meth)acrylate radicals. The following radicals may be mentioned as examples:

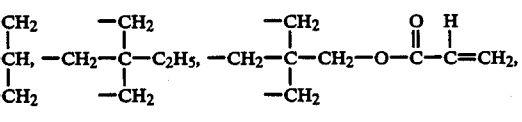

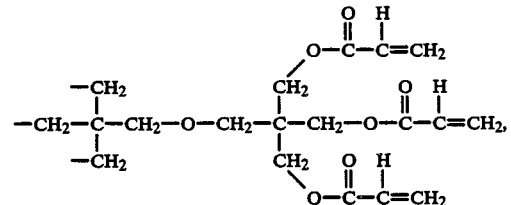

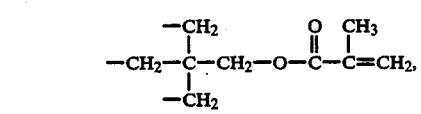

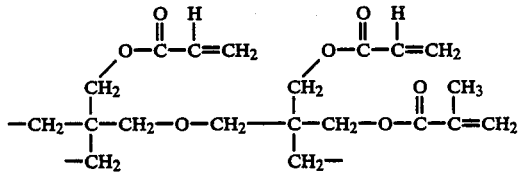

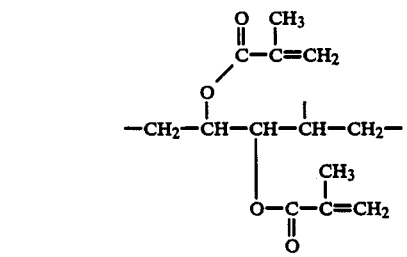

-continued

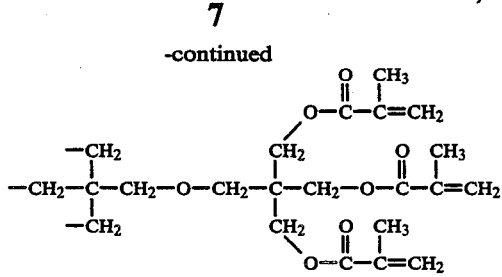

Those (meth)acrylic acid derivatives, containing urethane groups, of the formula (I) are preferred in which A is a straight-chain or branched aliphatic radical having 3 to 12 carbon atoms and optionally containing 1 to 3 oxygen bridges, an aromatic radical having 6 to 14 carbon atoms, an araliphatic radical having 7 to 26 carbon atoms or a cycloaliphatic radical having 6 to 14 carbon atoms, r represents the number of chains starting from A and denotes a number from 2 to 6, $R^1$ and $R^2$ are identical and denote hydrogen or are different and denote hydrogen and methyl, n denotes a number from 0 to 5, independently for each chain starting from A, X is a divalent, straight-chain or branched aliphatic radical having 2 to 12 carbon atoms, a monocycloaliphatic radical having 6 to 14 carbon atoms or an aromatic radical having 6 to 18 carbon atoms, it also being possible for 1 to 3 of the aliphatic, monocycloaliphatic or aromatic radicals to be linked via optionally substituted methylene groups, Z is a trivalent, straight-chain or branched aliphatic hydrocarbon radical having 3 to 10 carbon atoms, which can optionally contain 1 or 2 oxygen bridges and can optionally be substituted by 1 or 2 (meth)acrylate radicals, and $R^3$ denotes hydrogen or methyl, independently for each chain starting from A.

Those (meth)acrylic acid derivatives, containing urethane groups, of the formula (I) are particularly preferred in which A represents the 2,2-bismethylene-butan-1-yl radical, propane-1,2,3-triyl radical, 2,2-bismethylenepropane-1,3-diyl radical or 3(4),8(9)-bismethylenetricyclo[5.2.1.0$^{2.6}$]decane radical, r represents the number of chains starting from A and denotes the number 3 or 4, $R^1$ and $R^2$ are identical and denote hydrogen or are different and denote hydrogen and methyl, n denotes a number from 0 to 5, independently for each chain starting from A, X represents one of the radicals

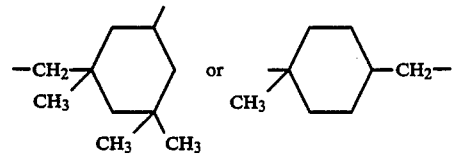

Z denotes a trivalent, straight-chain or branched aliphatic hydrocarbon radical which has 3 to 10 carbon atoms, can optionally contain 1 oxygen bridge and can optionally be substituted by 1 (meth)acrylate radical, and $R^3$ denotes hydrogen or methyl, independently for each chain starting from A.

The following (meth)acrylic acid derivatives containing urethane groups may be mentioned as examples:

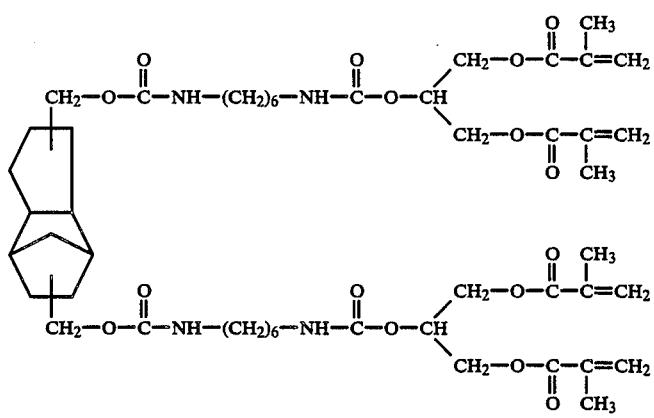

-continued
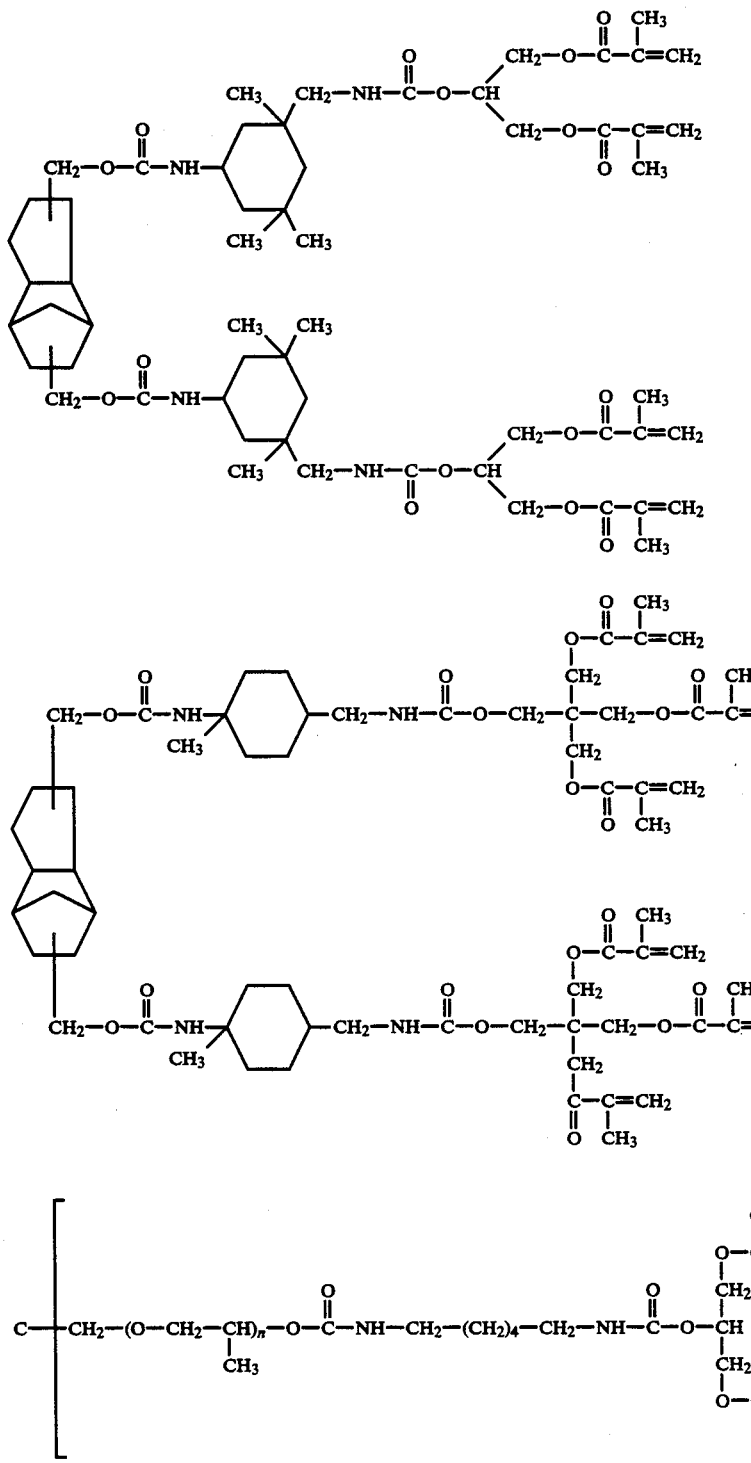
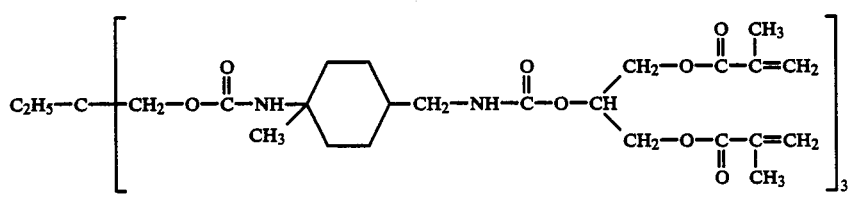

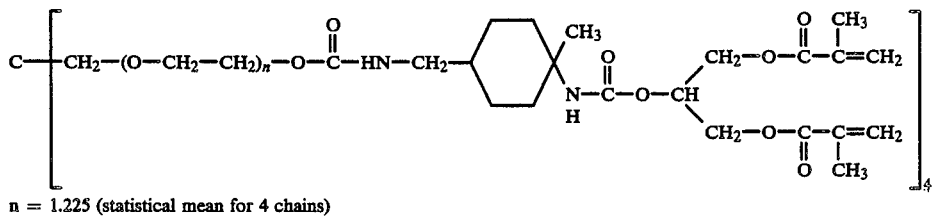

n = 1.225 (statistical mean for 4 chains)

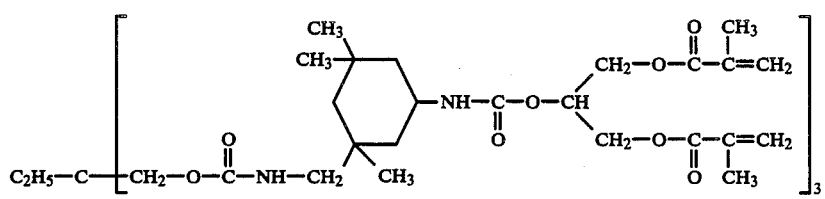

A process for the preparation of the (meth)acrylic acid derivatives, according to the invention, containing urethane groups, of the formula (I)

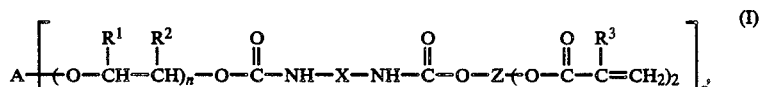

wherein
- A is a straight-chain or branched aliphatic radical having 2 to 20 carbon atoms and optionally containing 1 to 3 oxygen bridges, an aromatic radical having 6 to 24 carbon atoms, an araliphatic radical having 7 to 26 carbon atoms or a cycloaliphatic radical having 6 to 26 carbon atoms,
- r represents the number of chains starting from A and denotes a number from 2 to 6,
- $R^1$ and $R^2$ are identical and denote hydrogen or are different and denote hydrogen and methyl,
- n denotes a number from 0 to 5, independently for each chain starting from A,
- X denotes a divalent, straight-chain or branched aliphatic radical having 2 to 24 carbon atoms, an aromatic radical having 6 to 26 carbon atoms, an araliphatic radical having 7 to 26 carbon atoms or a monocycloaliphatic radical having 6 to 26 carbon atoms, it being possible for the aliphatic, aromatic, araliphatic and/or monocycloaliphatic radicals to contain 1 or 2 oxygen bridges and for several of the aliphatic, aromatic, araliphatic and/or monocycloaliphatic radicals to be linked via optionally substituted methylene groups,
- Z denotes a trivalent, straight-chain or branched aliphatic hydrocarbon radical which has 3 to 15 carbon atoms, can optionally contain 1 to 3 oxygen bridges and can optionally be substituted by 1 to 3 additional (meth)acrylate radicals, and
- $R^3$ denotes hydrogen or methyl, independently for each chain starting from A, has also been found, which is characterized in that a hydroxyalkyl (meth)acrylic acid ester of the formula (II)

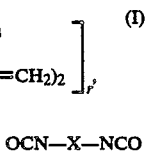

wherein

Z and $R^3$ have the meaning given above, is reacted with a diisocyanate of the formula (III)

OCN—X—NCO   (III), wherein
X has the meaning given above,
in a molar ratio of about 1:1 to 1:6 in an inert solvent in the presence of a catalyst and the isocyanatourethane formed is then, after the unconverted diisocyanate has been removed, reacted with a polyol of the formula (IV)

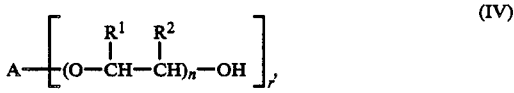

wherein
A, $R^1$, $R^2$, n and r have the meaning given above, in a molar ratio of OH groups to NCO groups of about 1:1.

(Meth)acrylic acid esters of the formula II are known per se and can be obtained, for example, by partial esterification of the corresponding polyols.

Diisocyanates of the formula III are known per se (European Patent 0,153,561) and can be prepared, for example, by reaction of the diamines with phosgene.

It can be advantageous to purify the resulting isocyanate-urethane, if the diisocyanate III was employed in an excess relative to the hydroxyalkyl (meth)acrylic acid ester II.

The purification of the isocyanate-urethane is preferably carried out by extraction with aliphatic solvents having boiling points below 120° C. under normal pressure, for example with pentane, n-hexane or isopentane.

Polyols of the formula IV are known per se (literature, for example, DE-A 2,931,925) or are commercially available, and they can be prepared, for example, by oxyalkylation of the known polyols of the formula A(OH)$_n$, for example 2,2-bishydroxymethylbutane, 2,2-bishydroxymethylpropane-1,3-diol, 3(4),8(9)-bishydroxymethyl-tricyclo[5.2.1.0$^{2,6}$]decane and the like.

Depending on the method of preparation, the polyols IV can also be in the form of a mixture of oxyalkylation products of a variable chain length.

Inert solvents are in general used for the process according to the invention. Acetone, chloroform, tetrahydrofuran, dioxane, methylene chloride, toluene and acetonitrile may be mentioned as examples. Chloroform, toluene, acetonitrile and acetone are particularly preferred.

In general, the process according to the invention is carried out with exclusion of water. A maximum quantity of water of less than 0.1% by weight, relative to the total quantity of the reactants, is particularly preferred.

The catalysts for the process according to the invention are in general metal salts of higher fatty acids. Preferred catalysts can, for example, be dibutyl-tin dilaurate, dibutyl-tin methoxide and tin(II) octoate. However, compounds with tertiary amino groups, such as triethylamine, pyridine, 2-methylpyridine, N,N-dimethylpiperazine and N,N-dimethyl-benzylamine can also be used as catalysts. Moreover, it is possible to employ titanium compounds such as tetrabutyl titanate.

In general, the catalyst will be employed in a quantity of 0.1 to 2.5% by weight, preferably 0.1 to 1.5% by weight, relative to the total quantity of the reactants.

In a preferred embodiment, the process according to the invention can be carried out in the presence of a polymerization inhibitor. Polymerization inhibitors are known per se (Ullmanns Enzyklopädie der techn. Chemie [Ullmann's Encyclopedia of Industrial Chemistry], 4th edition, Verlag Chemie Weinheim, Volume 8, pages 19–45). 2,6-Di-tert.-butyl-4-methylphenol, hydroquinone and hydroquinone monomethyl ether may be mentioned as examples.

It is also possible to use oxygen, for example atmospheric oxygen, which is passed into the reaction mixture, as the polymerization inhibitor.

In general, the polymerization inhibitor is employed in a quantity of 0.01 to 1.0% by weight, preferably of 0.1 to 0.2% by weight.

The first stage of the process according to the invention is in general carried out in the temperature range from 0° to 120° C., preferably from 30° to 70° C. The second stage of the process according to the invention is in general carried out in the temperature range from 0° to 120° C., preferably from 30° to 70° C.

The process according to the invention is in general carried out under normal pressure. It is also possible, however, to carry out the process according to the invention under a reduced or superatmospheric pressure (for example in the pressure range from 0.1 to 10 bar).

The process according to the invention can be carried out, for example, as follows:

The (meth)acrylic acid ester of the formula (II) and, if appropriate, the polymerization inhibitor are dissolved in the inert solvent and added dropwise to the diisocyanate (III), which may be in solution, with stirring. The catalyst is here added to one of the two reactants. The reactants are caused to react in a molar ratio of about 1:1 to 1:6 and taken to complete conversion of the OH groups or the corresponding conversion of the isocyanate groups. The conversion of the isocyanate groups can be monitored in a known manner by IR spectroscopy and/or by titration.

An excess of diisocyanate can subsequently be extracted with n-hexane, n-pentane or other aliphatic solvents having a boiling point below 120° C. (under normal pressure).

In the second stage of the process according to the invention, the isocyanatourethane obtained in the first stage is, if appropriate after extraction of any excess diisocyanate present, reacted with a polyol of the formula IV in such a way that the number of hydroxyl equivalents of the polyol approximately corresponds to the number of the NCO equivalents still present.

Preferably, 0.9/r to 1.1/r moles of the polyol IV are employed, relative to 1 mole of hydroxyalkyl (meth)acrylate II, r here having the above meaning of a number from 2 to 6.

The reaction is in general taken to complete conversion, so that neither free isocyanate nor polyol remain in the reaction mixture. When the conversion is complete, the reaction product is isolated by removal of the solvent. A preceding filtration or purification by means of adsorbents, for example active charcoal, bleaching earth, silica gel or aluminum oxide, is possible.

By the process according to the invention, a mixture of (meth)acrylic acid derivatives containing urethane groups is as a rule obtained, and these derivatives can be separated on adsorbents.

For the use, according to the invention, of the new urethane-(meth)acrylates in the dental field a separation of the reaction mixtures obtained is not required. The mixtures themselves can be used in an advantageous manner as a component of dental material, for example tooth-filling materials.

Using diisocyanates of different reactivity of the NCO group, however, it is entirely possible selectively to prepare the (meth)acrylic acid derivatives of the formula I, containing urethane groups, according to the invention. Diisocyanates suitable for this purpose are above all those which, in addition to a sterically unhindered, aliphatically bonded isocyanate group, contain sterically hindered, cycloaliphatically bonded isocyanate groups, the following being mentioned as examples:

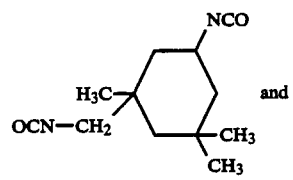

and

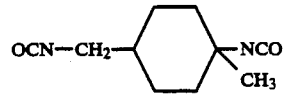

When using these diisocyanates, different reaction rates naturally result for the first and second synthesis stages.

It is also possible to invert the order of the first and second stages of the above process. In this case, the diisocyanate III and the polyol IV are reacted in the first stage in a molar ratio of NCO:OH=2 to 10, preferably in a molar ratio of NCO:OH=2.0 to 4, until all the hydroxyl groups have been converted to urethane groups. The excess of diisocyanate (if this was employed in an excess) which is present is then extracted with the solvents mentioned, in the manner described above. The remaining NCO groups are then reacted in the second stage with a hydroxyalkyl (meth)acrylate II to give the (meth)acrylic acid ester according to the invention. If diisocyanates are used of which the NCO groups have different reactivities due to steric hindrance, it is advatageous to adhere to a stoichiometry of NCO:OH=2.0–2.05 in the first stage.

In this process variant, particularly uniform products are obtained when diisocyanate of the formula

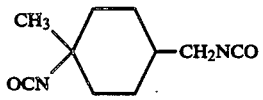

is used.

The urethane-(meth)acrylic acid derivatives according to the invention can be used in particular as monomers for dental materials. Filling materials for teeth, tooth coatings and components for tooth replacements, preferably plastic teeth, may be mentioned as examples of dental materials. Depending on the field of application, the dental materials can contain further additives.

For the use as monomers for polymerizable tooth-filling compositions or coatings in the dental field, the (meth)acrylic acid derivatives according to the invention can be mixed with monomers known per se, for example in order to match the viscosity to the intended use. In this case, viscosities in the range from 60 to 10,000 mPas are preferred. This can be accomplished by mixing the monomers according to the invention with, if appropriate, a comonomer of low viscosity as a relative diluent or solvent. In the mixture with monomers, the compounds according to the invention are in a proportion of about 30 to about 90% by weight, preferably of 40 to 80% by weight. It is also preferred to employ mixtures of different (meth)acrylic acid derivatives according to the invention.

In order to obtain the desired viscosity, it is also possible to employ monomer mixtures which contain several comonomers.

The following comonomers may be mentioned as examples: glycerol di(meth)acrylate, triethylene glycol di(meth)acrylate, tetraethylene glycol di(meth)acrylate, 1,12-dodecanediol di(meth)acrylate, 1,6-hexanediol di(meth)acrylate, diethylene glycol dimethacrylate, 2,2-bis-[p-(2'-hydroxy-3'-methacryloyloxypropoxy)-phenyl]-propane, 2,2-bis-[p-(2'-methacryloyloxyethoxy)-phenyl]-propane, trimethylolpropane tri(meth)acrylate, bis-(meth)acryloyloxyethoxymethyl-tricyclo[5.2.1.0$^{2.6}$]decane (DE-A 2,931,925 and DE-A 2,931,926).

Those comonomers are particularly preferred which have a boiling point above 100° C. under 13 mbar.

The polyfunctional (meth)acrylic acid esters according to the invention can, if appropriate as a mixture with the comonomers mentioned, be cured by methods known per se to give crosslinked polymers (Am. Chem. Soc., Symp. Ser. 212, 359-371 (1983)). For the so-called redox polymerization, a system comprising a peroxidic compound and a reducing agent, for example based on tertiary aromatic amines, is suitable. Examples of peroxides are: dibenzoyl peroxide, dilauroyl peroxide and di-4-chlorobenzoyl peroxide.

Examples of tertiary aromatic amines which may be mentioned are N,N-dimethyl-p-toluidine, bis-(2-hydroxyethyl)-p-toluidine, bis-(2-hydroxyethyl)-3,5-dimethylaniline and N-methyl-N-(2-methylcarbamoyloxypropyl)-3,5-dimethylaniline. The concentrations of the peroxide or the amine are advantageously selected such that they amount to 0.1 to 5% by weight, preferably 0.5 to 3% by weight, relative to the monomer mixture. The monomer mixtures containing peroxide or amine are stored separately until they are used.

The monomers according to the invention can also be caused to polymerize by exposure with UV light or visible light (for example in the wavelength range from 230 to 650 nm). Examples of suitable initiators for the photoinitiated polymerization are benzil, benzil dimethylketal, benzoin monoalkyl ethers, benzophenone, p-methoxybenzophenone, fluorenone, thioxanthone, phenanthrenequinone and 2,3-bornanedione (camphorquinone), optionally in the presence of activators having a synergistic effect, such as N,N-dimethylaminoethyl methacrylate, triethanolamine, 4-N,N-dimethylaminobenzenesulphonic acid diallylamide. The photopolymerization procedure is described, for example, in DE-A 3,135,115.

Apart from the initiators described above, light stabilizers and other stabilizers, known per se for this application, can be added to the (meth)acrylic acid derivatives according to the invention.

Light stabilizers are described by way of example in (Gachter, Muller, Taschenbuch der Kunstoff-Additive, [Handbook of Plastics Additives], 2nd edition, Carl Hanser Verlag). The following light stabilizers may be mentioned as examples: Cyasorb UV9 ®, Tinuvin P ®, Tinuvin 770 ®, Tinuvin 622 ® and Tinuvin 765 ®.

Other stabilizers are described by way of example in (Ullmanns Encyclopädie der technischen Chemie [Ullmann's Encyclopedia of Industrial Chemistry], 4th edition, Volume 8). The following stabilizers may be mentioned as examples: 2,6-di-tert.-butylphenol, 2,6-di-tert.-butyl-4-methylphenol, 2,6-di-octadecyl-4-methylphenol, 1,1'-methylene-bis-(naphth-2-ol) and others.

The light stabilizers and other stabilizers can each be employed in a quantity of 0.01 to 0.5 parts by weight, relative to 100 parts by weight of monomer mixture.

The monomer mixtures can be employed as coating agents (dental varnishes) without added fillers.

For the use as tooth-filling compositions, fillers are in general added to the monomer mixtures obtained. In order to be able to obtain a high degree of filling, monomer mixtures having a viscosity in the range from 60 to 10,000 mPas are particularly advantageous.

Preferably, inorganic fillers are added to the (meth)acrylic acid derivatives according to the invention. Examples which may be mentioned are rock crystal, cristobalite, fused quartz, highly disperse silica, aluminium oxide and glass ceramics, for example glass ceramics containing lanthanum and zirconium (DE-A 2,347,591). The inorganic fillers are preferably pretreated with an adhesion promoter in order to improve the bonding with the polymer matrix of the polymethacrylate. Adhesion promotion can be accomplished, for example, by a treatment with organosilicon compounds (Progress in Organic Coatings 11, 297-308 (1983)). Preferably, 3-methacryloyloxypropyl-trimethoxysilane is used. The fillers for the tooth-filling compositions according to the invention have in general a mean particle diameter of 0.01 to 100 μm, preferably of 0.03 to 50 μm and particularly preferably of 0.03 to 5 μm. It can also be advantageous to employ several fillers of different particle diameters and/or different silane contents side by side.

The proportion of filler in the tooth-filling composition is in general 5 to 85% by weight, preferably 50 to 80% by weight.

To prepare the tooth-filling compositions, the components are mixed, using commercially available kneading machines.

The proportion of the urethane-(meth)acrylates according to the invention in the tooth-filling compositions is in general 5 to 70% by weight, relative to the filling composition.

Surprisingly, the dental varnishes and tooth-filling compositions according to the invention show particularly small shrinkage on polymerization and good mechanical strengths, in particular a high hardness and excellent wear resistance.

The urethane-(meth)acrylic acid derivatives according to the invention can also be used as components in the preparation of tooth replacements.

In this case, the monomers according to the invention are combined with the normally used constituents known per se. Preferably, the monomers are employed as a mixture with alkyl methacrylates, such as methyl methacrylate. In addition, bead polymers known per se can also be added. To match the tooth color, known inorganic and organic color pigments and opacifying agents can be added. The use of light stabilizers and other stabilizers is also possible.

The plastic teeth are prepared by free-radical polymerization of the dental compositions with shaping.

Processing is possible both by means of injection methods and swaging methods and is in general carried out by the usual preparation methods for teeth, based on poly(methyl methacrylate), for example by thermal polymerization using polymerization initiators known per se, for example tose based on peroxides and azo compounds, such as dibenzoyl peroxide, dilauroyl peroxide, cyclohexyl percarbonate and azo-bis-isobutyronitrile. Mixtures of polymerization initiators having different decomposition temperatures are also highly suitable.

The dental materials prepared from the (meth)acrylic acid esters according to the invention are distinguished by a high resistance to mechanical stress and a high abrasion resistance.

EXAMPLE 1

Reaction of glycerol dimethacrylate with hexamethylene diisocyanate and bis(hydroxymethyl)-tricyclo[5.2.1.0$^{2.6}$]decane (TCD-DM)

22.8 g of a commercially available glycerol dimethacrylate, 0.1 g of dibutyl-tin-dilaurate and 20 mg of 2,6-di-tert.-butyl-4-methylphenol (ionol) are dissolved in 50 ml of dried toluene and slowly added dropwise at 50° C. to 16.8 g of hexamethylenediisocyanate, air being passed through the reaction batch. The mixture is then stirred at 50° C. (about 3 hours) until half the NCO groups have been converted. The NCO groups are determined in a known manner by reaction with excess dibutylamine and back-titration with hydrochloric acid. 19.6 g of TCD-DM, dissolved in 30 ml of dried chloroform, are then added dropwise and the mixture is stirred (about 18 hours) until isocyanate is no longer detectable by IR-spectroscopy.

The reaction mixture is filtered over active charcoal and freed of solvent by evaporation. This gives a highly viscous liquid.

EXAMPLE 2

Reaction of glycerol dimethacrylate with isophorone diisocyanate and bis-(hydroxymethyl)-tricyclo[5.2.1.0$^{2.6}$]decane Example 1 was repeated, with the exception that 22.2 g of isophorone diisocyanate were used in place of hexamethylene diisocyanate and a reaction time of 28 hours was maintained in the second reaction stage. This gives a white solid.

EXAMPLE 3

Reaction of glycerol dimethacrylate with 1,6-hexamethylene diisocyanate and pentaerythritol 45.6 of commercially available glycerol dimethyacrylate, 0.1 g of dibutyl-tin dilaurate and 34 mg of ionol are dissolved in 50 ml of dried acetone and added dropwise at 45°–50° C. to 33.6 g of hexamethylene diisocyanate. The mixture is stirred at this temperature until half the NCO groups have reacted.

6.8 g of pentaerythritol in 50 ml of acetone are then added. The mixture is stirred (for about 48 hours) at 50° C. until isocyanate is no longer detectable in the IR spectrum. The reaction product is filtered over active charcoal and freed of solvent. Molecular weight (osmometric): 1620 (calculated: 1720) 200 MHz $^1$H-NMR spectrum in CDCl$_3$/TMS [ppm]:

6.12/5.6 (=CH$_2$, m, 16H)

5.2–5.3 (CH—O—, m, 4H)

4.2–4.4 (—O—CH$_2$—C(H)(O—)—CH$_2$—O—, m, 16H)

4.08 [(—O—CH$_2$)$_4$—C, S, 8H)

3.05–3.2 (—CH$_2$—N(H)(CO—O—), t, 16H)

1.92 (—C(=CH$_2$)—CH$_3$, m, 24H)

1.75 (—NH—, 8H)

1.4–1.55/1.2–1.4 (—(CH$_2$)$_4$—, m, 32H

EXAMPLE 4

Reaction of glycerol dimethacrylate with 1,6-hexamethylene diisocyanate and propoxylated pentaerythritol 45.6 of glycerol dimethacrylate, 39 mg of ionol and 0.1 g of dibutyl-tin dilaurate are dissolved in 50 g of dried acetone, added dropwise to 33.6 g of hexamethylene diisocyanate and stirred at 45°–50° C., until half the NCO groups have reacted (about 3 hours). An NCO content of 6.5 percent by weight was determined by titration with dibutylamine and HCl.

20.1 g of an adduct of 4.9 mole of propylene oxide and 1 mole of pentaerythritol, dissolved in 50 ml of acetone, are then added. The reaction temperature of 45°–50° C. is maintained until the NCO groups have been fully converted (check by IR spectroscopy).

After the reaction has ended, the mixture is filtered through silica gel and the solvent is stripped off in a rotary evaporator. The product is highly viscous, colorless liquid.

EXAMPLE 5

21.0 g of an adduct of 1 mole of pentaerythritol and 4.9 moles of propylene oxide (OH number=534) and 5 mg of ionol are heated to 100° C. in 100 ml of toluene. At this temperature, 38.8 g of 4-isocyanatomethyl-1-isocyanato-1-methyl-cyclohexane are added dropwise with stirring. The reaction mixture is stirred for about 46 hours at 100° C. until the conversion of the primary isocyanate groups is complete. After cooling to 40°–50° C., 45.6 g of commercially available glycerol dimethacrylate and 0.1 g of tin octoate are added. The mixture is stirred at 50° C. until the tertiary isocyanate groups have been fully converted and the solvent is removed (after filtration over active charcoal) under $10^{-2}$ mm Hg and at room temperature.

The product is a colorless, highly viscous liquid.

EXAMPLE 6

Application tests

The urethane-(acrylates) from Examples 1–4 and, for comparison purposes, monomer $A_1$ from Example 1 of British Patent 2,074,590 were diluted with triethylene glycol dimethacrylate (TEGDMA) and activated with 0.5% of N,N-dimethylaminobenzenesulphonic acid bis-allylamide, 0.2% of camphorquinone and 0.125% of benzil dimethylketal. The % data relate to the sum of urethane-(meth)acrylate and triethylene glycol dimethacrylate. The activated mixtures were cured by means of a commercially available dental lamp (Translux, from Messrs. Kulzer) to give solid specimens.

Using these specimens, the flexural strength was determined according to DIN 13,922 and a hardness test according to the Wallace method was carried out.

The Wallace method serves for determining the indentation hardness of plastics. A Vickers diamond is applied under an initial load of 1 p to the surface and then loaded for 60 seconds with a main load of usually 100 p. As a measure of the indentation resistance, the indentation depth of the diamond under the main load is measured. In contrast to the measurements of the Vickers or Brinell hardness, where the test force is related to the dimensions of the permanent indentation, the elastic deformation and the permanent deformation of the plastic are covered by the Wallace method.

This method is more suitable for the characterization of materials for applications in the dental field than hardness tests which cover only the permanent deformation. The smaller the penetration depth $H_W$, the harder is the material.

| Urethane-(meth)-acrylate | TEGDMA content % | Flexural strength [N/mm$^2$] | $H_w$ [μm] |
|---|---|---|---|
| Monomer $A_1$ according to British Patent 2,074,590 (comparison example) | 21.9 | 74 | 17.5 |
| Example 1 | 36.8 | 83 | 14.1 |
| Example 2 | 45.7 | 87 | 13.7 |
| Example 3 | 45 | 95 | 13.0 |

EXAMPLE 7

Preparation of plastic teeth 60 parts by weight of a monomer mixture, which was prepared from 45% by weight of triethylene glycol dimethacrylate and 55% by weight of the urethane-methacrylic acid derivative from Example 4, are mixed with 1 part by weight of dibenzoyl peroxide and 40 parts by weight of a highly disperse silica which has been silanized with 5% of 3-methacryloyloxypropyl-trimethoxysilane (BET surface area: 50 m$^2$/g).

The activated mixture is injected into a tooth mould and cured at 130° C. within 6 minutes. The plastic teeth obtained show a particularly high abrasion resistance.

What is claimed is:

1. A dental material containing a (meth)acrylic acid derivative containing urethane groups, of the formula $$A\left[\left(O-\underset{R^1}{\underset{|}{C}H}-\underset{R^2}{\underset{|}{C}H}\right)_n O-\overset{O}{\underset{\|}{C}}-NH-X-NH-\overset{O}{\underset{\|}{C}}-O-\right.$$
$$\left.-Z\left(O-\overset{O}{\underset{\|}{C}}-\underset{R^3}{\underset{|}{C}}=CH_2\right)_2\right]_r$$

wherein

A is a straight-chain or branched aliphatic radical having 2 to 20 carbon atoms in a carbon chain and optionally containing 1 to 3 oxygen bridges, an aromatic radical having 6 to 24 carbon atoms, an araliphatic radical having 7 to 26 carbon atoms or a cycloaliphatic radical having 6 to 26 carbon atoms, r represents the number of chains starting from A and denotes a number from 2 to 6, $R^1$ and $R^2$ are identical and denote hydrogen or are different and denote hydrogen and methyl, n denotes a number from 0 to 5, independently for each chain starting from A, X is a divalent, straight-chain or branched aliphatic radical having 2 to 24 carbon atoms in a carbon chain, an aromatic radical having 6 to 26 carbon atoms in a carbon chain, an araliphatic radical having 7 to 26 carbon atoms in a carbon chain or a monocycloaliphatic radical having 6 to 26 carbon atoms in a carbon chain, it being possible for the aliphatic, aromatic, araliphatic and/or monocycloaliphatic radicals to contain 1 to 2 oxygen bridges and for several of the aliphatic, aromatic, araliphatic and/or monocycloaliphatic radicals to be linked via optionally substituted methylene groups, Z denotes a trivalent straight-chain or branched aliphatic hydrocarbon radical which has 3 to 15 carbon atoms in a carbon chain and can optionally contain 1 to 3 oxygen bridges and can optionally be substituted by 1 to 3 (meth)acrylate radicals, and $R^3$ denotes hydrogen or methyl, independently for each chain starting from A and an effective amount of either a free radical polymerization initiator or a photoinitiator.

2. A dental material according to claim 1, comprising in addition to the (meth)acrylic and derivative containing urethane groups further comonomers said comonomers having a boiling point about 100° C. under 13 m bar.

3. A dental material according to claim 2 further comprising fillers.

4. In a method of filling teeth using as the filling material a (meth)acrylic acid derivative and an inorganic filler, the improvement comprising filling said teeth with the dental material according to claim 1.

5. In a method of coating teeth using as the coating material a (meth)acrylic acid derivative, the improvement comprising coating said teeth with the dental material according to claim 1.

6. In a method of preparing a tooth replacement based on polymers of (meth)acrylic acid derivatives comprising forming said tooth replacement from a dental material containing a (meth)acrylic acid derivative and polymerizing, the improvement wherein the dental material is the material according to claim 1.

7. A polymer of a (meth)acrylic acid derivative containing urethane groups, of the formula

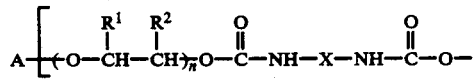

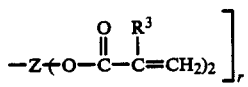

wherein
- A is a straight-chain or branched aliphatic radical having 2 to 20 carbon atoms in a carbon chain and optionally containing 1 to 3 oxygen bridges, an aromatic radical having 6 to 24 carbon atoms, an araliphatic radical having 7 to 26 carbon atoms or a cycloaliphatic radical having 6 to 26 carbon atoms,
- r represents the number of chains starting from A and denotes a number from 2 to 6,
- $R^1$ and $R^2$ are identical and denote hydrogen or are different and denote hydrogen and methyl
- n denotes a number from 0 to 5, independently for each chain starting from A,
- X is divalent, straight-chain or branched aliphatic radical having 2 to 24 carbon atoms in a carbon chain and, an aromatic radical having 6 to 26 carbon atoms in a carbon chain and, an araliphatic radical having 7 to 26 carbon atoms in a carbon chain and or a monocycloaliphatic radical having 6 to 26 carbon atoms in a carbon chain and, it being possible for the aliphatic, aromatic, araliphatic and/or monocycloaliphatic radicals to contain 1 or 2 oxygen bridges and for several of the aliphatic, aromatic, araliphatic and/or monocycloaliphatic radicals to be linked via optionally substituted methylene groups,
- Z denotes a trivalent straight-chain or branched aliphatic hydrocarbon radical which has 3 to 15 carbon atoms in a carbon chain and can optionally contain 1 to 3 oxygen bridges and can optionally be substituted by 1 to 3 (meth)acrylate radicals, and
- $R^3$ denotes hydrogen or methyl, independently for each chain starting from A.

* * * * *

UNITED STATES PATENT AND TRADEMARK OFFICE
CERTIFICATE OF CORRECTION

PATENT NO. : 4,952,241

DATED : August 28, 1990

INVENTOR(S) : Reiners et al.

It is certified that error appears in the above-identified patent and that said Letters Patent is hereby corrected as shown below:

Title Page [54] After " (METH) " delete " ACYLIC " and substitute -- ACRYLIC --

Col. 1, line 1 of title  After "(METH) " delete "ACYLIC " and substitute -- ACRYLIC --

Col. 21, line 9  Delete " about " and substitute -- above --

Col. 22, lines 23, 24, 26, & 27  Delete " and "

Signed and Sealed this

Fourteenth Day of July, 1992

Attest:

DOUGLAS B. COMER

Attesting Officer

Acting Commissioner of Patents and Trademarks